(12) United States Patent
Briseboi et al.

(10) Patent No.: US 6,685,020 B2
(45) Date of Patent: Feb. 3, 2004

(54) VISUAL REFERENCE SYSTEM FOR SANITARY ABSORBENT ARTICLE

(76) Inventors: Henri Briseboi, 2129 Florent, Lachenaie, Quebec (CA), J6W 5W6; Roya Mohmad, 5975 Place de l'Authion, Apt. 504, Montreal, Quebec (CA), H1M 2W3

(*) Notice: Subject to any disclaimer, the term of this patent is extended or adjusted under 35 U.S.C. 154(b) by 0 days.

(21) Appl. No.: 10/165,974

(22) Filed: Jun. 10, 2002

(65) Prior Publication Data

US 2002/0148749 A1 Oct. 17, 2002

Related U.S. Application Data

(62) Division of application No. 09/569,667, filed on May 12, 2000, now Pat. No. 6,454,095.

(51) Int. Cl.⁷ .............................................. B65D 85/00
(52) U.S. Cl. .................................. 206/440; 206/459.5
(58) Field of Search ............................... 206/233, 440, 206/459.1, 459.5, 494, 581, 812; 40/312

(56) References Cited

U.S. PATENT DOCUMENTS

| | | | | |
|---|---|---|---|---|
| 654,545 A | * | 7/1900 | Johnson | 40/312 |
| 1,683,487 A | * | 9/1928 | Ramlley | 206/440 |
| 2,054,033 A | * | 9/1936 | Ford | 206/459.5 |
| 2,750,033 A | * | 6/1956 | Pickens | 206/440 |
| 3,306,437 A | * | 2/1967 | Nelson | 206/459.5 |
| 3,351,209 A | * | 11/1967 | Kofed et al. | 206/459.5 |
| 5,036,978 A | * | 8/1991 | Frank et al. | 206/494 |
| 5,366,087 A | * | 11/1994 | Bane | 206/459.5 |
| 5,524,758 A | * | 6/1996 | Lupul | 206/459.5 |
| 5,725,311 A | * | 3/1998 | Ponsi et al. | 206/494 |
| 5,725,382 A | * | 3/1998 | Walter et al. | 206/459.5 |
| 5,931,304 A | * | 8/1999 | Hammond | 206/459.5 |
| 5,967,665 A | * | 10/1999 | MacDonald et al. | 206/494 |
| 6,454,095 B1 | * | 9/2002 | Brisebois et al. | 206/494 |

FOREIGN PATENT DOCUMENTS

| | | | |
|---|---|---|---|
| CH | 466791 | * | 12/1968 |
| GB | 696381 | * | 8/1953 |
| WO | 97/45088 | * | 12/1997 |
| WO | 00/13632 | * | 3/2000 |

* cited by examiner

*Primary Examiner*—Jim Foster

(57) ABSTRACT

A receptacle containing a plurality of sanitary absorbent articles that are individually packaged. On each package is applied a visual reference system. The visual reference system includes a first and a second elements of information. The first element of information is indicative of a scale of reference establishing a range of values of a certain characteristic of the sanitary absorbent article in the package. The second element of information is indicative of a certain degree or level on the scale of reference. The certain characteristic can be the liquid absorption capacity of the sanitary absorbent article.

20 Claims, 6 Drawing Sheets

VISUAL REFERENCE SYSTEM FOR SANITARY ABSORBENT ARTICLE

This is a divisional application of U.S. patent application Ser. No 09/569,667, filed on May 12, 2000, now U.S. Pat. No. 6,454,095.

FIELD OF THE INVENTION

The present invention relates to sanitary absorbent articles such as feminine sanitary napkins, incontinence pads, panty liners, tampons and diapers among others and, more particularly, to sanitary absorbent articles featuring a visual reference system that allows the user to quickly ascertain a characteristic of the sanitary absorbent article, such as the liquid absorption capacity, the configuration, and the type of material used in the manufacture of the sanitary absorbent article, among others. Under a different aspect, the invention provides a reminder tag that can facilitate the selection and purchase of a sanitary absorbent article by the user in a place where sanitary articles are offered for sale.

BACKGROUND OF THE INVENTION

Sanitary absorbent articles are large-scale commercially manufactured articles used to absorb and retain bodily exudates. Such articles are convenient in that they are economical yet disposable; they include sanitary napkins, infant diapers, adult incontinence pads, panty liners, tampons and the like.

Sanitary absorbent articles and particularly feminine sanitary napkins are made available to the consumer in receptacles containing a plurality of sanitary napkins. Traditionally, the industry has used receptacles in the form of cardboard boxes. In more recent years the cardboard box has gradually been replaced by a bag of plastic material. The sanitary napkins held in a receptacle, either a cardboard box or a bag of plastic material are individually packaged. This feature allows the user to transport a sanitary napkin outside the protective environment of the receptacle, such as in a purse or pocket, while keeping the sanitary napkin free from dirt, stains or impurities. The typical packaging is in the form of a pouch of plastic material in which the sanitary napkin is placed. Immediately before use, the wearer removes the sanitary napkin from the pouch and installs it in the crotch portion of the undergarment. The pouch is then discarded.

A user normally keeps at home a supply of sanitary napkins having different characteristics to meet the different requirements that may arise during the menstrual cycle. For example, during light menstrual days, the user will normally employ a sanitary napkin of a comparatively small liquid absorption capacity. Such a sanitary napkin has a reduced size and is comfortable to wear. During heavier menstrual flow days, the user will wear a larger sanitary napkin that offers an increased liquid absorption capacity. During the night, the user may elect to use sanitary napkins designed especially for nighttime. Nighttime products are longer and offer an exceptionally high liquid absorption capacity. At the end of the menstrual cycle or between menstrual cycles, the user will rely on a panty liner designed to retain primarily vaginal discharges other than menstrual liquid.

In addition to the various levels of liquid absorption capacity, sanitary napkins can be functionally distinguished from one another on the basis of other characteristics, such as their configuration and the materials used for their construction. For example, sanitary napkins are available with or without flaps. When a sanitary napkin has flaps, the flaps can be folded about the crotch portion of the undergarment to aid in stabilizing the sanitary napkin in use. Sanitary napkins having different geometrical shapes or forms exist to better fit the anatomy of the wearer. Finally, sanitary napkins with different types of body contacting layers are available to suit the preferences of the consumers. In particular, some users prefer a body-contacting layer made of fibrous material while others prefer a body-contacting layer made of polymeric film.

The wide variety of sanitary napkins that are presently available in the marketplace has the undesirable effect of confusing the consumer. This problem is compounded by ever increasing product diversification. Different manufacturers offer different product brands featuring unique characteristics. Although this approach provides sanitary napkins that are precisely tailored to the needs of the user, the identification of the product that best meets the individual needs becomes a challenge.

A particular problem occurs when the user carries in her purse or pocket one or more individually packaged sanitary napkins. Since the packaging (pouch) found on sanitary napkins today is opaque, a simple visual inspection of the pouch will not reveal to the user the characteristics of the sanitary napkin in the package, such as its liquid absorption capacity, configuration or type of material used in the construction of the sanitary napkin, among others. The user is left with the option of removing the sanitary napkin from the pouch to ascertain if it is of the type she now requires. However, the removal of the sanitary napkin from the pouch usually results in the destruction of the pouch. If it turns out that the sanitary napkin is of a type unsuitable for the immediate need, the sanitary napkin is wasted.

To alleviate this problem, manufacturers have in the past applied on individually packaged sanitary napkins a written notice that informs the user of the liquid absorption capacity of the sanitary napkin. In theory, such written notice should suffice to provide the user with the information she seeks on the level of liquid absorption of the sanitary napkin. In practice, this is not always the case since manufacturers use different terminology to designate different levels of liquid absorption. For instance, one manufacturer may use wording like "light", "normal" and "heavy" while a different manufacturer may prefer the terminology "mini", "regular" and "super". Accordingly, a written notice alone is of somewhat abstract nature to the user and fails to provide the user with precise information on the liquid absorption capacity.

Considering this background, it clearly appears that there is a need in the industry to develop an improved visual reference system that would permit the user to more easily identify a certain characteristic of a sanitary absorbent article.

SUMMARY OF THE INVENTION

Under a first broad aspect, the present invention provides a receptacle holding a plurality of sanitary absorbent articles, at least one of the sanitary absorbent articles being placed in an individual package. The individual package includes a visual reference system. The visual reference system includes two elements of information, namely a first element of information and a second element of information. The first element of information is indicative of a scale of reference establishing a range of values of a certain characteristic of the sanitary absorbent article in the individual package. The second element of information is indicative of a certain degree or level on the scale of reference.

The advantage of the visual reference system resides in the additional information provided to the user by the scale of reference. The scale of reference provides a context into which the second element of information is more meaningful than when the second element of information is presented alone.

The first and the second elements of information are realized by creating markings on the package such as to make the first and the second elements of information visually perceptible and understandable by the user. The intended information can be delivered to the user in a number of ways, such as in the form of a written notice, in the form of pictographs (iconic symbols) or a combination of both. In a non-limiting example of implementation, the first element of information may be a collection of words, each word expressing a certain degree on the scale of reference. The second element of information points to a particular degree on the scale of reference. This can be achieved by highlighting the word in the collection of words that corresponds to the particular degree.

The markings can be applied on the package by printing, embossing, die-cutting, application of a discrete label on which the markings are realized or, in general, by any other physical change in the form or character of the package such as to make the markings visually noticeable and understandable to the user.

In a specific non-limiting example of implementation, the first and the second elements of information are related to the absorbency characteristics of the sanitary absorbent article, in particular the liquid absorption capacity of the sanitary absorbent article. The first element of information defines a range of liquid absorption capacities while the second element of information points toward a certain degree or level on that range.

Under a second broad aspect, the invention provides a receptacle holding a plurality of sanitary absorbent articles, at least one of the sanitary absorbent articles is placed in an individual package. The individual package includes an element of information representative of a characteristic of the sanitary absorbent article, the characteristic being selected in the group consisting of the geometrical configuration of the sanitary absorbent article and a material used in the manufacture of the sanitary absorbent article. In a specific non-limiting example of implementation, the sanitary absorbent article is a sanitary napkin. The element of information conveys to the user information regarding the arrangement or formation of the parts of the sanitary napkin, such as whether the sanitary napkin has flaps or whether the sanitary napkin is flat or curved, among other possibilities. In a variant, the element of information informs the user about the type of material from which the body contacting layer of the sanitary napkin is made, in particular fibrous material or polymeric film. In another variant, the element of information communicates to the user a certain characteristic of the material used in the manufacture of the external layer of the sanitary napkin (usually called "barrier layer" or "barrier sheet"). In particular, this characteristic can be whether the external layer is breathable or not.

Under a third broad aspect, the invention provides a receptacle holding a plurality of sanitary absorbent articles, at least one of the sanitary absorbent articles is placed in an individual package. A removable reminder tag is associated with the receptacle. The reminder tag has a substrate on which is realized an element of information. A matching element of information is realized on an external surface of the receptacle. When the user wants to purchase sanitary absorbent articles from the store, she takes with her the reminder tag from the empty receptacle at home. The user selects the proper brand and category of sanitary absorbent articles simply by locating the receptacle on the shelves that has an element of information matching the element of information on the reminder tag.

In a non-limiting example of implementation, the reminder tag is a discrete label. The reminder tag is associated with the receptacle by removably affixing the label to the individual package placed in the receptacle. This can be effected by using adhesive on the label that establishes a non-permanent bond with the individual package. Alternatively, the reminder tag is associated with the receptacle by placing the reminder tag within the receptacle without affixing it to any one of the sanitary absorbent articles, nor to the receptacle walls. In another variant, the association between the reminder tag and the receptacle is made by making the reminder tag as part of the receptacle itself. Under this possibility, the reminder tag could be delineated by tear lines that assist the user in separating the tag from the remainder of the receptacle, or the reminder tag could be delineated by a scissors-line, such as a dotted line printed on the receptacle indicating to the user where to cut the wall of the receptacle with scissors so as to free the reminder tag.

The element of information realized on the reminder tag can be descriptive of one or more characteristics of the sanitary absorbent article. For instance, the element of information can specify either in writing, by pictographs (iconic symbols) or a combination of both the liquid absorption capacity of the sanitary absorbent article, the arrangement or formation of the parts of the sanitary absorbent article and information pertaining to the type of materials used in the construction of the sanitary absorbent article. Alternatively, the element of information can be totally abstract and provide only a mark that the user can visually associate with a corresponding mark on the receptacle to establish a match.

BRIEF DESCRIPTION OF THE DRAWINGS

A detailed description of examples of implementation of the present invention is provided hereinbelow with reference to the following drawings, in which.

Figure 1:
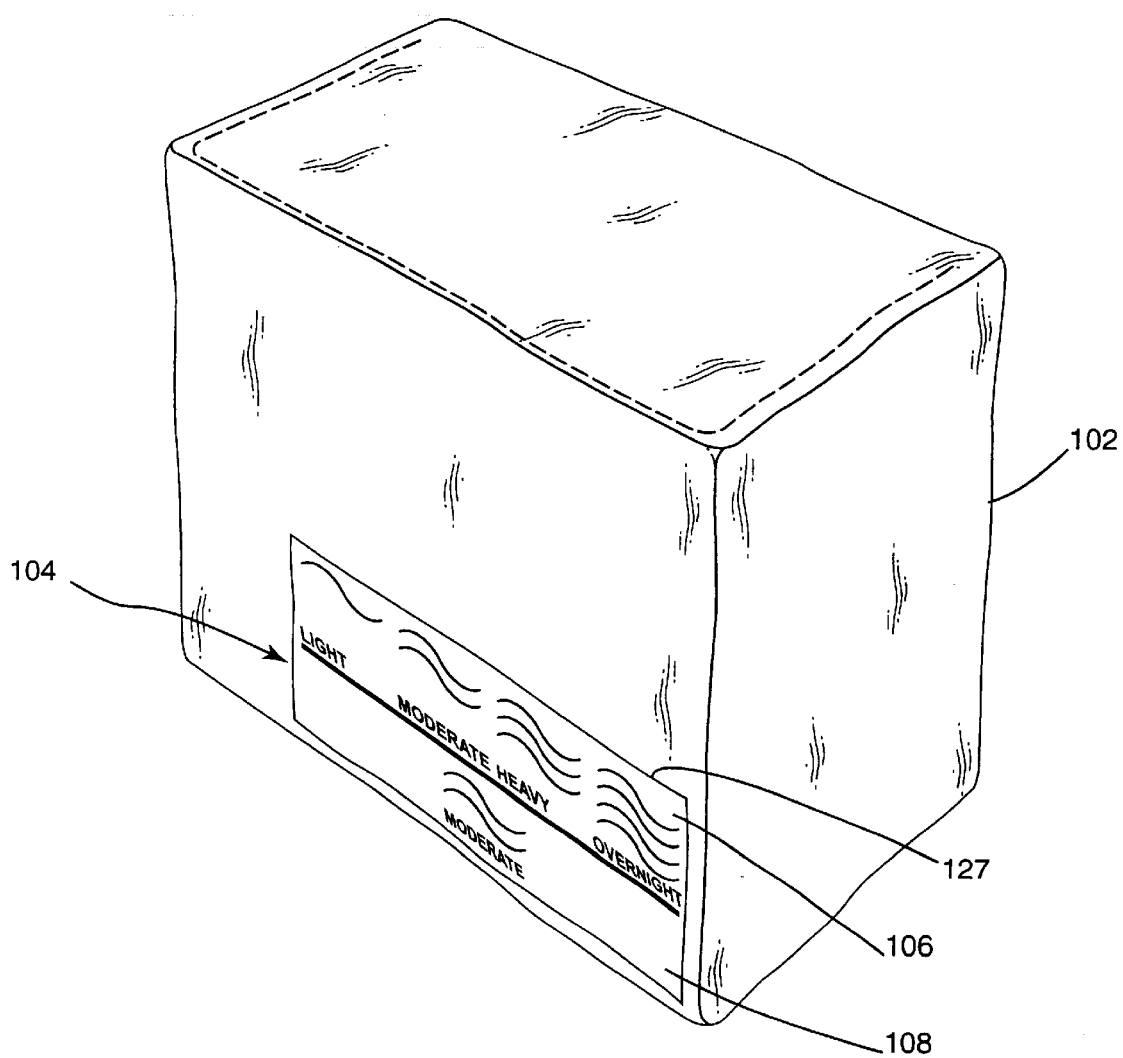
FIG. 1 is a perspective view of an unopened receptacle containing sanitary napkins.

In the drawings, embodiments of the invention are illustrated by way of example. It is to be expressly understood that the description and drawings are only for purposes of illustration and as an aid to understanding, and are not intended to be a definition of the limits of the invention.

DETAILED DESCRIPTION

With reference to FIG. 1, there is shown a non-limiting example of implementation of the present invention. FIG. 1 illustrates a receptacle designated by the reference numeral 102 holding a plurality of sanitary napkins. The receptacle 102 is in the form of a flexible bag made of synthetic material such as plastic film. Other forms of packaging can be used without departing from the spirit of the invention. Examples of these other forms could be a cardboard box or any other suitable structure that can physically hold a plurality of sanitary napkins.

Figure 2:
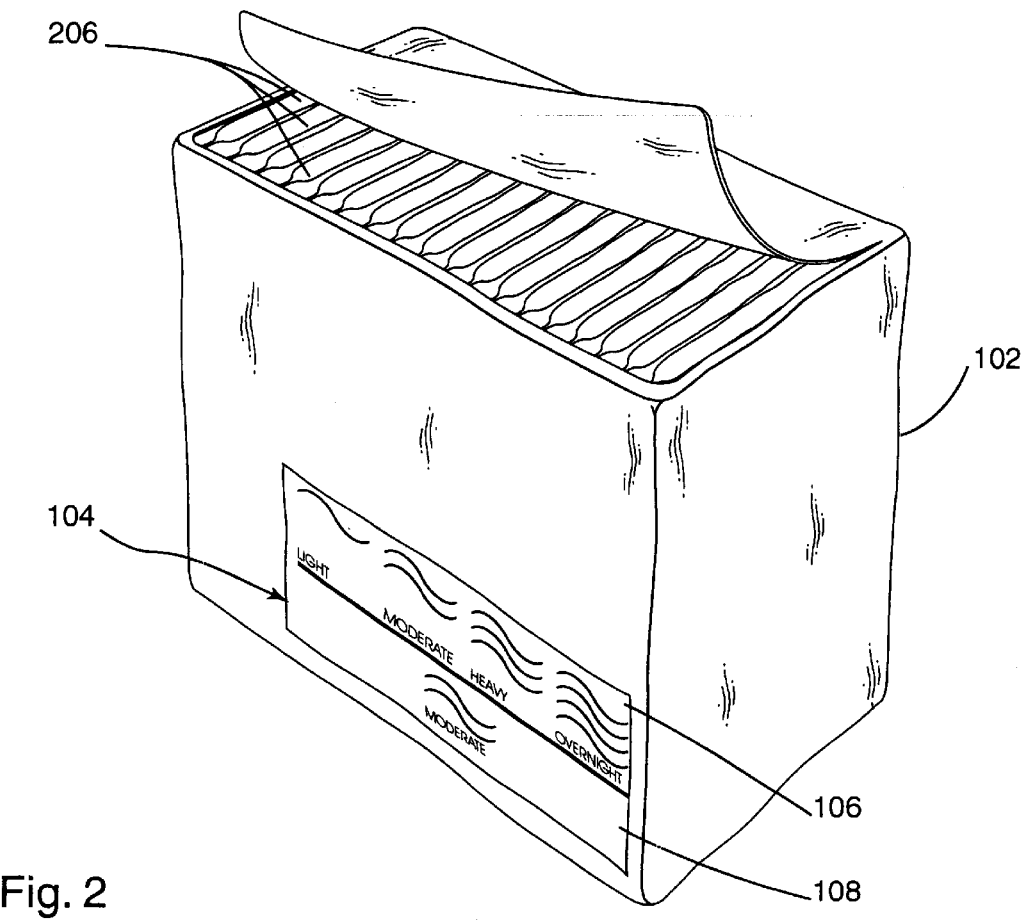
FIG. 2 is a perspective view of the receptacle of FIG. 1, the receptacle being now opened to expose a plurality of individually packaged sanitary napkins.

FIG. 2 shows the receptacle 102 after it has been opened to access the sanitary napkins inside. The receptacle 102 holds a plurality of sanitary absorbent napkins 206 wrapped in individual pouches.

Figure 3:
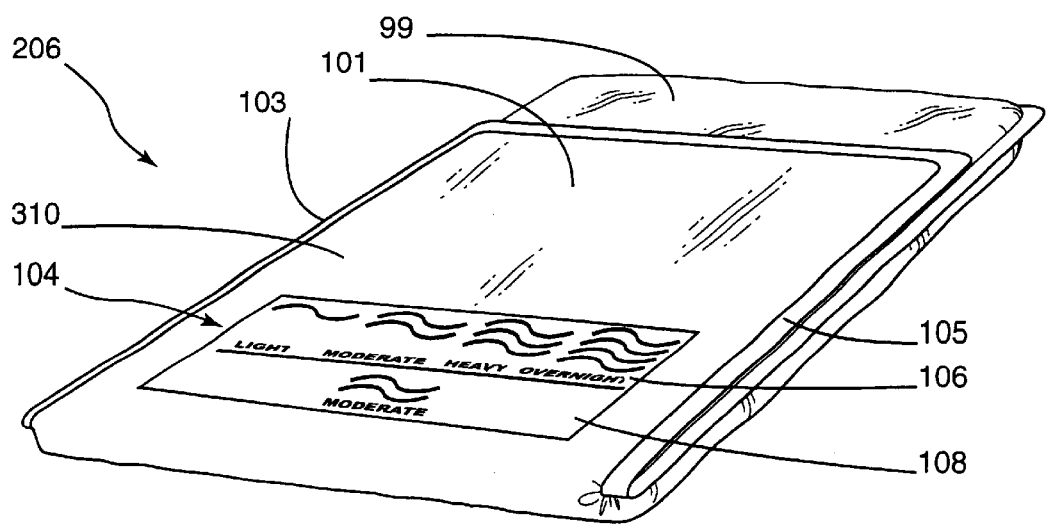
FIG. 3 is a perspective view of an individually packaged sanitary napkin provided with the visual reference system in accordance with the invention.

FIG. 3 illustrates a single sanitary napkin 206 removed from the receptacle 102 and stored in a pouch 310. The pouch is made from a sheet of synthetic material folded such as to completely enclose the sanitary napkin 206 and protect the sanitary napkin 206 when the user carries the sanitary napkin 206 in her purse or pocket. Other forms of packaging can also be considered to form the pouch 310 without departing from the spirit of the invention. Examples of these other forms of packaging include paper wrapping or any other suitable material or structure that could hold the sanitary napkin 206. The pouch 310 shown in FIG. 3 comprises a section forming an envelope-like enclosing structure 99 in which the sanitary napkin 206 is placed in a folded condition. A flap 101 closes the envelope-like enclosing structure 99. The flap 101 and the envelope-like enclosing structure 99 are united to one another by adhesive, crimping or sealing at their longitudinal edges, 103, 105 such as to keep the flap 101 in a closed position. When the user wishes to remove the sanitary napkin from the pouch 310, she pulls on the flap 101 to break the bond between the flap 101 and the envelope-like enclosing structure 99 and thus open the envelope-like enclosing structure 99.

The pouch 310 shown in FIG. 3 comprises a visual reference system 104. The visual reference system 104 carries two elements of information. The first element of information 106 is a scale of reference that establishes a range of values of a certain characteristic of the sanitary napkin 206. The other element of information 108 acts as a pointer, defining a position, level or degree on the scale of reference 106.

In the non-limiting example of implementation depicted in FIG. 3, the visual reference system 104 is related to the absorbency characteristics of sanitary napkins and in particular it expresses the liquid absorption capacity of the sanitary napkin 206. The first element of information 106 is comprised of a series of four icons, each icon including wave-like symbols, the number of wave-like symbols denoting the level of liquid absorbency. In particular, the higher the number of wave-like symbols in the icon, the higher the liquid absorption capacity. The first element of information 106 also comprises a written notice including a set of words or labels that communicate to the user in writing the different liquid-absorption capacities on the reference scale. There is one word or label associated with each icon. In the example shown in the drawings, the set of words or icons is "light", "moderate", "heavy" and "overnight".

The second element of information 108 includes an icon of wave-like symbols associated to a word or label expressing in writing the level of liquid-absorption capacity of the sanitary napkin 206 in the pouch 310. The first element of information 106 establishes a context in which the significance of the second element of information 108 can be precisely appreciated. For instance, the first element of information 106 indicates to the user that the sanitary napkin 206 is available in four different liquid-absorption capacities. The second element of information 108 indicates that the sanitary napkin 206 in the pouch 310 is at the second level on the reference scale in the direction of increasing liquid-absorption capacity.

The visual reference system 104 can be realized by creating markings on the receptacle 102 that render the first and second elements of information 106, 108 readily visible to the user. In the example of implementation depicted in FIG. 3, the markings are created by a printing process. Alternatively, the markings can be created on the pouch by embossing, die-cutting, application of a separate stick-on tab or label or any other suitable method. The application of the markings by embossing presents the advantage of allowing the markings to be understood by the sense of touch. This is useful for blind people or in dark environments where there is not enough light to read the markings.

Figure 4:
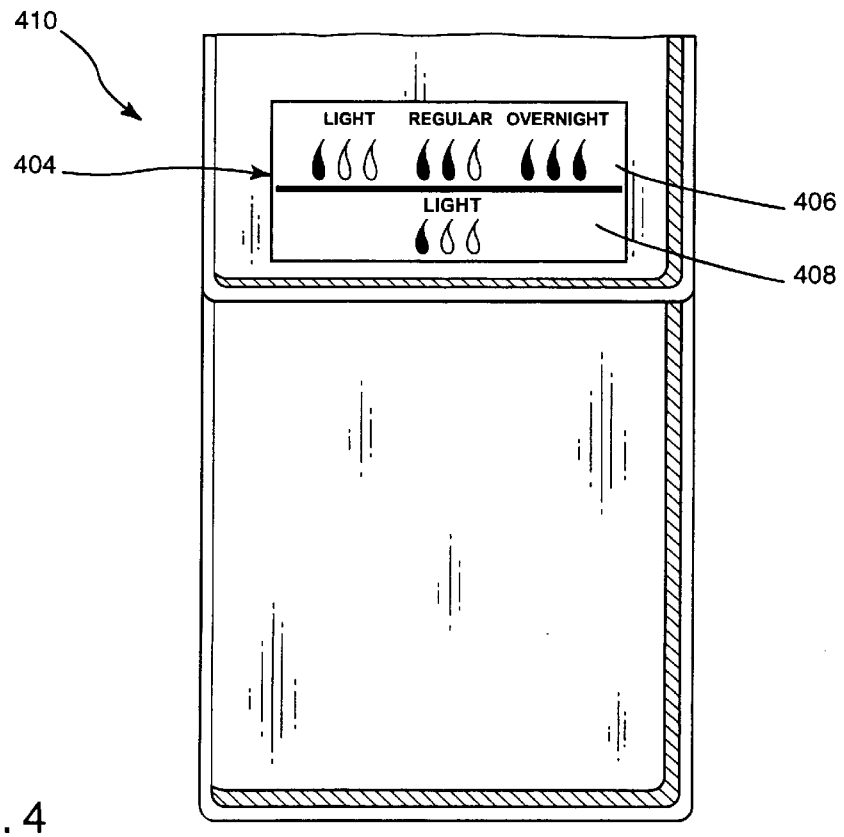
FIG. 4 is a top plan view of an individually packaged sanitary napkin provided with a visual reference system in accordance with a first variant.

FIG. 4 depicts an individually packaged sanitary napkin 410 with a visual reference system 404 according to a variant. The first element of information 406 or scale of reference in this embodiment is comprised of a series of three icons wherein each icon includes three symbols in the shape of liquid drops. The number of darkened drops denotes the liquid-absorption capacity of the sanitary napkin 410. In particular, the higher the number of darkened drops, the higher the liquid-absorption capacity. The first element of information 406 also comprises a written notice including a set of words or labels that communicate, in writing to the user the different liquid-absorption capacities on the reference scale. There is one word or label associated with each icon. In the example shown in FIG. 4, the set of words is "light", "regular" and "overnight". The second element of information 408 points to a particular degree on the scale of reference.

Figure 5:
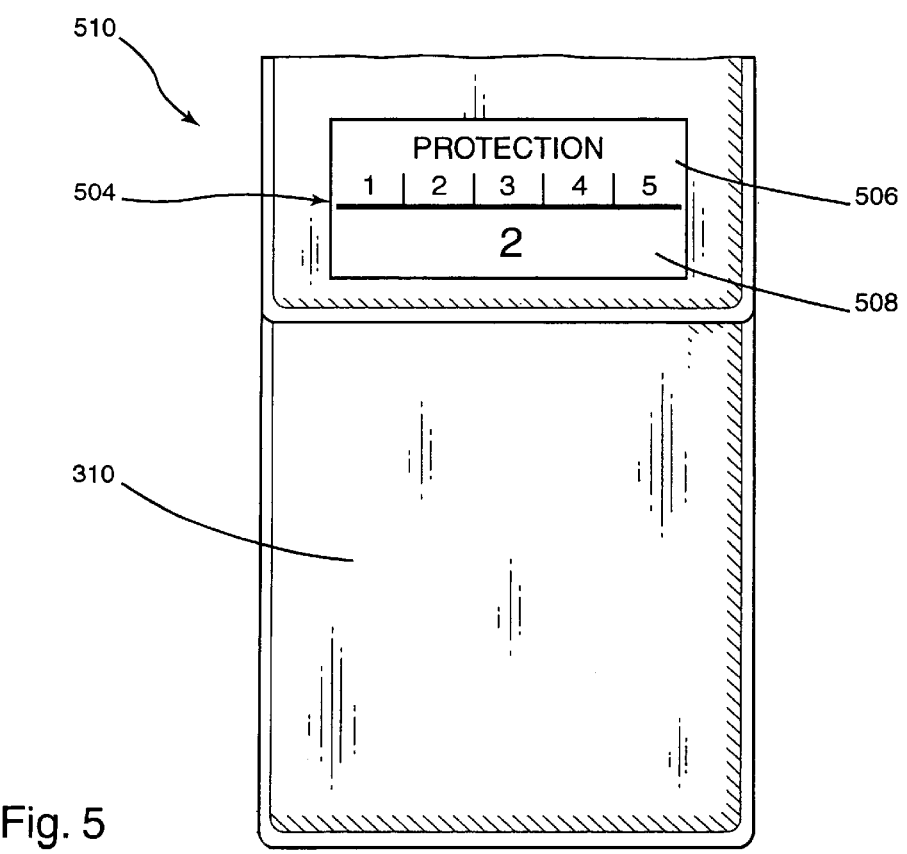
FIG. 5 is a top plan view of an individually packaged sanitary napkin provided with a visual reference system in accordance with a second variant.

FIG. 5 depicts an individually packaged sanitary napkin 510 with a visual reference system 504 according to another variant. The first element of information 506 is comprised of a series of numbers from 1 to 5, the value of the number denoting the liquid-absorption capacity of the sanitary napkin 510. More specifically, the higher the number, the greater the liquid-absorption capacity of the sanitary napkin 510. The second element of information 508 includes a single number, between 1 and 5, that expresses the liquid-absorption capacity of the sanitary napkin 510 contained within the pouch 310.

Figure 6:
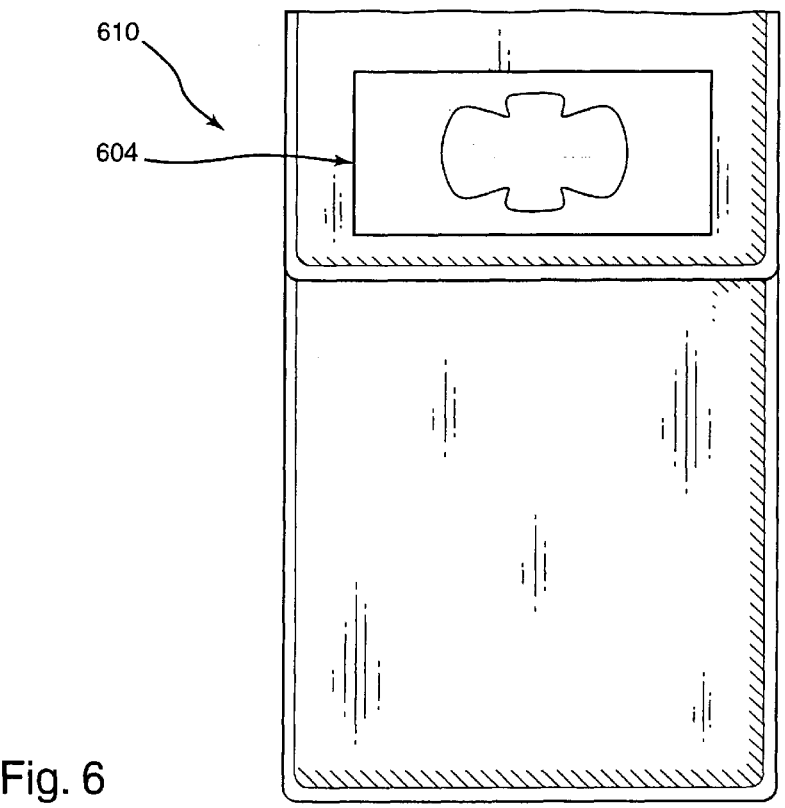
FIG. 6 is a top plan view of an individually packaged sanitary napkin provided with a visual reference system in accordance with a third variant.

FIG. 6 depicts an individually packaged sanitary napkin 610 with a visual reference system 604 according to yet another variant. The visual reference system 604 is related to the configuration of the sanitary napkin 610. The element of information conveyed by the visual reference system 604 is comprised of an icon depicting a specific geometrical configuration of the sanitary napkin 610. The icon pertaining to FIG. 6 shows a sanitary napkin 610 with flaps. Alternatively, the icon could depict a sanitary napkin without flaps indicating to the user that the sanitary napkin in the pouch 610 is of the flapless variety.

In yet another possible variant, not shown in the drawings, the visual reference system indicates to the user whether the sanitary napkin is flat or curved. A curved sanitary napkin is a product that normally acquires a certain curvature in a vertical plane that contains the longitudinal axis of the sanitary napkin. One possible way to create the curvature is to provide the sanitary napkin with elasticized longitudinal sides. In contrast, a flat sanitary napkin is a product that has no mechanisms or means designed to impart a curvature to the body of the sanitary napkin.

In yet another possible variant, not shown in the drawings, the visual reference system is descriptive of the type of material or the characteristics of the material used in the manufacture of the sanitary napkin. In one specific, non-limiting example the visual reference system is related to the type of material used in the construction of the body-contacting layer of the sanitary napkin. As it is well known to those skilled in the art, a sanitary napkin is constructed from different layers of materials. On the top of the sanitary napkin is provided a fluid-pervious body-contacting layer (usually called "cover layer"). Immediately below the body contacting layer is provided an absorbent system. Under the absorbent system is provided a liquid-impervious layer (usually called "barrier layer"). The barrier layer normally faces the undergarment of the user when the sanitary napkin is worn. Under a first possibility, the visual reference system indicates to the user the material used in the construction of the body-contacting layer, whether fibrous material of apertured polymeric film. Under a different possibility, the visual reference system indicates to the user the characteristics of the material used for the construction of the barrier layer, in particular whether the barrier layer is breathable or not breathable. A breathable material is a material that allows vapor to pass through it while blocking the passage of liquid.

For additional information on the structure of a sanitary napkin the reader is invited to refer to the U.S. Pat. Nos. 5,718,699 and 5,868,727 both assigned to Johnson & Johnson Inc. These two patents describe examples of sanitary napkins using the layered construction described earlier.

Figure 7:
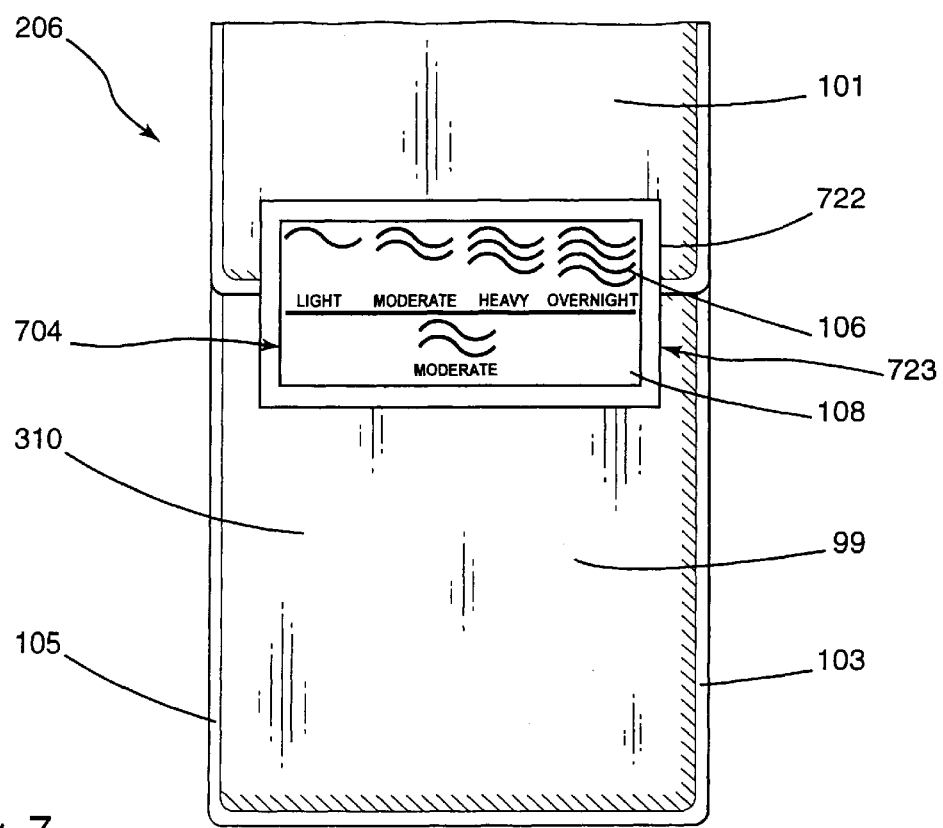
FIG. 7 is a top plan view of an individually packaged sanitary napkin provided with an adhesive reminder tag on which is realized a visual reference system in accordance with the invention.

FIG. 7 shows a further variant of the embodiment of the invention illustrated in FIG. 3. The pouch 310 shown in FIG. 7 comprises a visual reference system 704 that has two elements of information that are the same as those described in connection with FIG. 3. However, in this embodiment, the visual reference system 704 is realized on a substrate 722 that is adhesively attached to the pouch 310, extending partly on the flap 101 and partly on the envelope-like enclosing structure 99. The adhesive generally used is of a type such as to create a weak and temporary bond so that the user can remove the substrate 722 without tearing the substrate 722 or the material of the pouch 310. Such adhesives are well known to those skilled in the art and they do not need to be described in detail here.

The substrate 722 forms a convenient closure device that keeps the flap 101 closed prior to the use of the sanitary napkin 206. Under this embodiment, the longitudinal sides of the flap 101 and the longitudinal sides of the envelope-like enclosing structure 99 do not need to be bonded to one another.

Once the flap 101 has been opened, the substrate 722 can be peeled-off completely to form a reminder tag 723 that can assist the user in the purchase of sanitary napkins from the store.

Individually packaged sanitary napkins 206 are sold to consumers in the receptacle 102 depicted in FIG. 1. According to one embodiment of this invention, the receptacle 102 carries on its external surface an indicia 127 that can be visually matched with the reminder tag 723. When the user needs to buy sanitary napkins, she takes the reminder tag 723 in her purse or pocket to the store. It then suffices for the user to locate on the shelf of the store the receptacle with the indicia 127 that matches the reminder tag 723. This system permits to easily identify the type of sanitary napkin the user normally purchases, without the need of remembering details such as the particular brand, absorption characteristics, configuration, materials used in the construction of the sanitary napkin etc.

It should be noted that it is not essential that the information on the reminder tag 723 be identical to the indicia 127 for them to match. What is required is that the element of information on the reminder tag 723 is related in appearance, nature, sense or significance to the indicia 127 so that a user can rapidly create an association between them.

Although the embodiment shown in FIG. 7 depicts the reminder tag 723 adhesively placed on the pouch 310, straddling the flap 101 and the envelope-like enclosing structure 99, it is to be expressly understood that the positioning of the adhesive reminder tag 723 anywhere along the body of the pouch 310 falls within the scope of the present invention.

Figure 8:
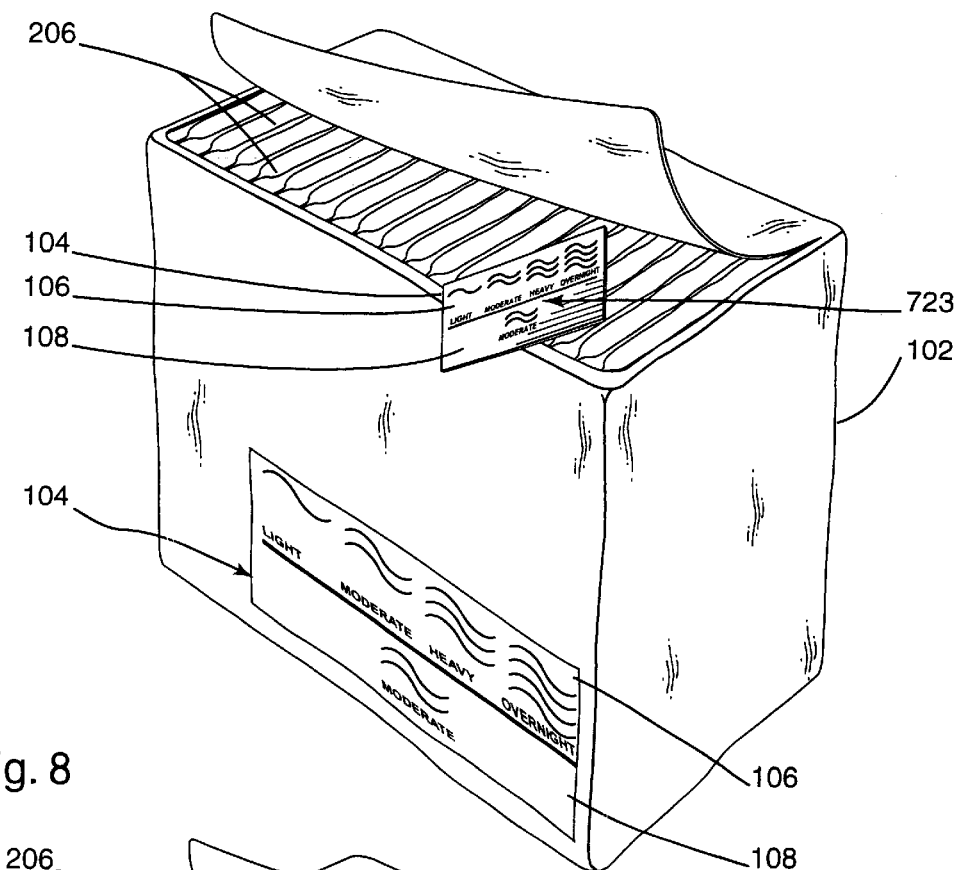
FIG. 8 is a perspective view of a receptacle, containing a plurality of sanitary napkins, the receptacle being opened to expose a plurality of individually packaged sanitary napkins and a reminder tag that is loosely placed in the receptacle.

FIG. 8 depicts a variant in which the reminder tag 723 is loosely placed within the receptacle 102 without being attached to any one of the individually packaged sanitary napkins 206. Thus, the reminder tag 723, freely floating within the receptacle 102, is readily accessible to the user once the receptacle 102 is opened. This implies that the user can, at any time, remove the reminder tag 723 from the receptacle 102 and place it in her pocket or purse for future reference.

Figure 9:
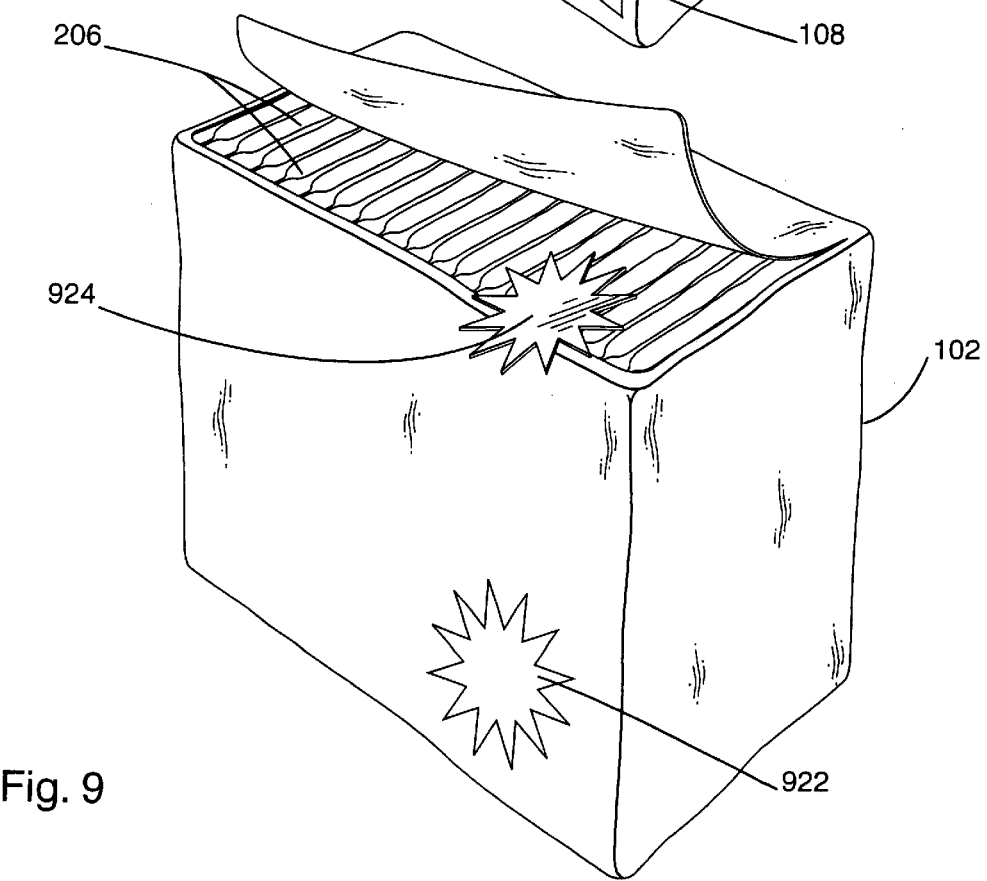
FIG. 9 is a perspective view of a receptacle containing a plurality of sanitary napkins, the receptacle being opened to expose a plurality of sanitary napkins and a reminder tag that is loosely placed in the receptacle, the reminder tag being characterized by a symbol of abstract nature.

FIG. 9 depicts yet another possible variant in which the reminder tag 924 contains a purely abstract element of information. In particular, the reminder tag 924 is in the shape of a sun or star. Although the reminder tag 924 in FIG. 10 has the shape of a sun or star, any other type of abstract symbol can be used. Moreover, the same abstract symbol 922 is also realized on the outer surface of the receptacle 102 that houses the corresponding sanitary napkins 206. The user can thereby easily associate the shape of the reminder tag 924 that is contained within her purse or pocket to the symbol 922 on the outer surface of the receptacle 102 on the shelves in the store.

Figure 10:
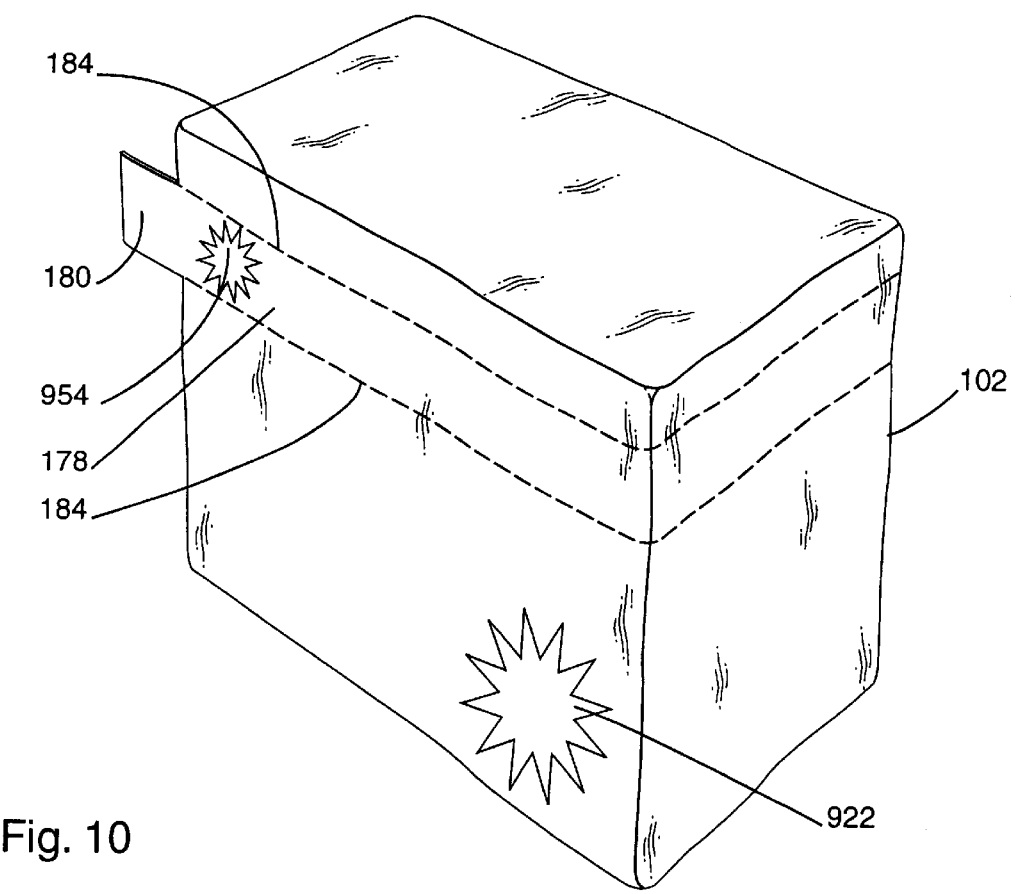
FIG. 10 is a perspective view of a receptacle for storing sanitary napkins including a tear-away strip on which the reminder tag is realized.

FIG. 10 depicts another variant in which the receptacle 102 is characterized by a tear-away strip 178 that extends along the top walls of the receptacle 102. The tear-away strip's 178 main purpose is to facilitate the opening of the receptacle 102 so that the user can readily access the sanitary napkins contained therein. At one of its extremities, the tear-away strip 178 has a pull-tab 180. The tear-away strip is defined by lines of weakness 184 such as perforation lines. In this specific example, the reminder tag 954 is realized on a section of the tear-away strip 178. Consequently, the user, upon opening the receptacle 102, can easily detach the reminder tag 954 and immediately store it in her purse or pocket for future reference.

Figure 11:
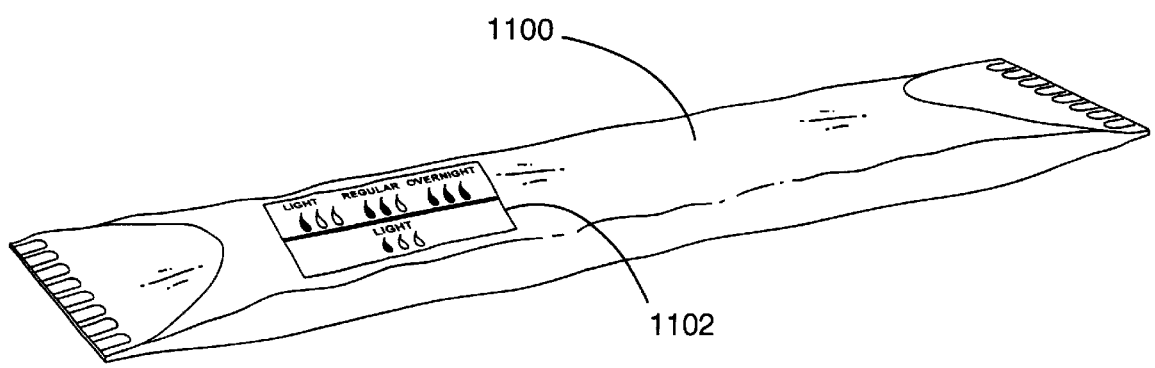
FIG. 11 is a top plan view of a tampon in an individual pouch to which is realized the visual reference system in accordance with the invention.

FIG. 11 illustrates another embodiment of the present invention. A pouch 1100 contains a tampon. The pouch is provided with a visual reference system 1102 similar to the visual reference system 404 illustrated in FIG. 4.

Although various embodiments have been illustrated, this was for the purpose of describing, but not limiting, the invention. Various modifications will become apparent to those skilled in the art and are within the scope of this invention, which is defined more particularly by the attached claims.

What is claimed is:

1. A receptacle holding a plurality of sanitary absorbent articles;
   at least one sanitary absorbent article placed in an individual package, said individual package including an element of information representative of a characteristic of said at least one sanitary absorbent article, said characteristic being selected from the group consisting of the configuration of said at least one sanitary absorbent article and the material used in the manufacture of a component of said at least one sanitary absorbent article.

2. A receptacle as defined in claim 1, wherein said at least one sanitary absorbent article is selected in the group consisting of sanitary napkin, incontinence pad, panty liner, and diaper.

3. A receptacle as defined in claim 2, wherein said element of information is realized by markings realized on said individual package, said markings conveying information that is visually perceptible by a user.

4. A receptacle as defined in claim 3, wherein said element of inn includes a constituent selected from the group consisting of written notice, pictograph, and a combination of written notice and pictograph.

5. A receptacle as defined in claim 4, wherein said markings are applied on said individual package by a process selected from the group consisting of printing, embossing, die-cutting and application of a separate label on said individual package on which said markings are realized.

6. A receptacle as defined in claim 5, wherein said element of information conveys to the observer information whether said sanitary napkin has flaps.

7. A receptacle as defined in claim 5, wherein said sanitary napkin includes a plurality of layers that are superposed to one another, one of said layers being a layer that contacts a body of a user when said sanitary napkin is worn by the user, said element of information conveys to the observer information about a material of said layer that contacts the body of the user.

8. A receptacle as defined in claim 7, wherein said element of information communicates to the user whether the material of said layer that contacts the body of the user is made of fibrous material.

9. A receptacle as defined in claim 7, wherein said element of information communicates to the user whether the material of said layer that contacts the body of the user is made of apertured polymeric film.

10. A receptacle as defined in claim 5, wherein said element of information conveys to the observer information whether said sanitary napkin is curved.

11. A receptacle as defined in claim 5, wherein said sanitary napkin a plurality of layers that are superposed to one another, one of said layers being an external layer that faces an undergarment of a user when said sanitary napkin is worn by the user, said element of information conveys to the user information whether said external layer is breathable.

12. A receptacle holding a plurality of sanitary absorbent articles,
    at least one sanitary absorbent article placed in an individual package;
    a removable reminder tag comprised of a substrate on which is realized a first element of information;
    an external surface comprising a second element of information matching said first element of information;
    said reminder tag being removably affixed to said individual package.

13. A receptacle as defined in defined in claim 12, wherein said is adhesively affixed to said individual package.

14. A receptacle as defined in claim 13, wherein said at least one absorbent article is selected in the group consisting of sanitary napkin, incontinence pad, panty liner, and diaper.

15. A receptacle holding a plurality of sanitary absorbent articles placed in individual packages, comprising:
    a removable reminder tag comprised of a substrate on which is realized a first element of information;
    an external surface comprising a second element of information matching said first element of information;
    said reminder tag being enclosed in said receptacle and said reminder tag is unattached to any one of the individual packages.

16. A receptacle as defined in claim 15, wherein said at least one sanitary absorbent article is selected in the group consisting of sanitary napkin, incontinence pad, panty liner, and diaper.

17. A receptacle holding a plurality of sanitary absorbent articles, comprising:
    at least one sanitary absorbent article placed in an individual package;
    a removable reminder tag on which is realized a first element of information;
    an external surface comprising a second element of information matching said first element of information;
    said reminder tag being on the external surface of said receptacle.

18. A receptacle as defined in claim 17, including a tear line extending along at least a portion of said reminder tag.

19. A receptacle as defined in claim 18, including a tear-away portion, said tear away portion being delineated by at least one tear line, said tear away portion being separable from the receptacle to allow access to an interior of said receptacle, said tear away portion being separable from said receptacle as a result of a pull applied to said tear away portion, said reminder tag being on said tear-away portion.

20. A receptacle as defined in claim 19, wherein said tear-away portion is shaped as a strip.

* * * * *